US005705198A

United States Patent [19]
Triplett et al.

[11] Patent Number: 5,705,198
[45] Date of Patent: Jan. 6, 1998

[54] TEST FOR LUPUS ANTICOAGULANT

[75] Inventors: Douglas A. Triplett, South Muncie, Ind.; Kurt Stocker, Aesch, Switzerland

[73] Assignee: Pentapharm AG, Basel, Switzerland

[21] Appl. No.: 471,796

[22] Filed: Jun. 6, 1995

Related U.S. Application Data

[62] Division of Ser. No. 983,341, Nov. 30, 1992, Pat. No. 5,453,370.

[30] Foreign Application Priority Data

Sep. 4, 1992 [EP] European Pat. Off. .............. 92810679

[51] Int. Cl.$^6$ ........................................... A61K 35/58
[52] U.S. Cl. ............................................ 424/542; 436/69
[58] Field of Search ........................ 424/94.67, 529, 424/542, 9.1; 530/856; 435/212, 219, 288.4; 436/69

[56] References Cited

U.S. PATENT DOCUMENTS

| | | | |
|---|---|---|---|
| 4,106,992 | 8/1978 | Varirel et al. | 195/66 B |
| 4,725,673 | 2/1988 | Herring | 530/381 |
| 5,112,949 | 5/1992 | Vukovich | 530/380 |
| 5,192,689 | 3/1993 | Heinker et al. | 435/13 |
| 5,219,995 | 6/1993 | Herzog et al. | 530/381 |

OTHER PUBLICATIONS

Triplett et al. Clinical application of a functional array for protein C. Hematologic Pathology, 1 (4), 239–248. 1987.
Alving et al. Comparison between a one–point dilute phospholipid APTT and the dilute Russell Viper Venom time verification of Lupus Anticoagulants. Thrombosis and Haemostasis.67(6), 672–678. 1992.
D.A. Triplett et al., "Lupus Anticoagulants: Misnomer, Paradox, Riddle Epiphenomenon," Hematol. pathol. 2, 121–143, 1988.
P.E. Love et al., "Antiphospholipid Antibodies: Anticardiolipin and the Lupus Anticoagulant in Systemic Lupus Erythematosus (SLE) and in Non–SLE Disorders," Ann. Int. Med. 112, 682–698, 1990.
T. Exner et al., SSC Subcommittee for the Standardization of Lupus Anticoagulants, "Guidelines for Testing and Revised Criteria for Lupus Anticoagulants," Thromb. Haemost. 65, 320–322, 1991.
J. Rosing et al., "Inventory of Exogenous Prothrombin Activators," Thrombosis and Haemostasis 65, 627–630, 1991.
P.P. Masci et al., "Purification and Characterization of a Prothrombin Activator from the Venom of the Australian Brown Snake, Pseudonaja Textilis Textilis," Biochemistry International, 17, 825–835, 1988.
C.Y. Lee (ed.), Snake Venoms, pp. 15–40, Springer Verlag, Berlin, Heidelberg, New York (1979).

H. Hofmann et al., "Blood Coagulation Induced by the Venom of Bothrops atrox. 1. Identification, Purification, and Properties of a Prothrombin Activator," Biochemistry, 26, 772 (1987).
Journal of Biological Chemistry, vol. 261, No. 28, 5 Oct. 1986, pp. 13258–13267, H. Speijer et al. "Prothrombin Activation by an Activator from the Venom of Oxyuranus scutellatus (Taipan Snake)".
Thrombosis and Haemostasis, vol. 65, No. 3, 4 Mar. 1991, Stuttgart De, pp. 320–322, T. Exner et al., "Guidelines for Testing and Revised Criteria for Lupus Anticoagulants".
Thrombosis Research, vol. 3(6), 1973, pp. 705–714, G.G. Owen et al.
Thrombosis Research, vol. 1(6), 1972, pp. 559–568.
Govers–Rienslag, J.W.P. et al., "Haemostology", vol. 7, 1988, pp. 41–53, editor H. Pirkle et al., Marcel Dekko Inc., NY.
Thrombosis and Haemostasis, Speijer, H. et al., vol. 57(3), 1987 (Jun.), pp. 349–355.
Thrombosis and Haemostasis, vol. 42(1), Jul. 1979, p. 4000. #0954–abstract, Owen, W.G. et al.
Aust. N.Z.J. Med., vol. 18(3, s–pp1 #2), 1988, p. 430, abstract, Whitaker, AN etal.
Scopes, R.K. Protein Purification—Principles and Procedure, 2nd edition, pp. 1, 17–20, 41–42, pp. 50–54 Springer–Verlog, 1987.
Deutscher, M.P. (ed.), Methods in Enzymology, vol. 182—Guide for protein Purification, Academic Process, Inc., 1990, p. 285, pp. 292–295.
Fohlman, J., "Toxican", vol. 17, 1979, pp. 170–172.
Tibbals, J., "Anaesth Intro Core", vol. 20(1), Feb. 1992, pp. 28–32.
Chester A. et al., Toxicon, vol. 20 (2), 1982, pp. 501–504.
Lalloo, O. et al., Toxicon, vol. 30(5–6), 1992, p. 528.
Masci, PP et al., Thrombosis Research, vol. 59, 1990, pp. 859–870.
Walker, F.J. et al. Biochemistry, vol. 19, 1980, pp. 1020–1023.
Nakagak, T. et al., Thrombosis Research, vol. 65, 1992, pp. 105–116.
T. Morita et al., "Purification and Properties of Prothrombin Activator from the Venom of Echis carinatus", J. Biochem. 83, 559–570 (1978).

Primary Examiner—Jean C. Witz
Attorney, Agent, or Firm—Pennie & Edmonds

[57] ABSTRACT

It was found that the use of a phospholipid dependent prothrombin activator purified from the venom of snakes belonging to the Elapidae family, especially members of the Oxyaranus and Psuedonaja genera is most useful in tests for the determination of Lupus Anticoagulant. Based on this, several clotting, chromogenic aria immunochromogenic tests have been developped.

18 Claims, No Drawings

TEST FOR LUPUS ANTICOAGULANT

This is a division of application Ser. No. 07/983,341, filed Nov. 30, 1992 now U.S. Pat. No. 5,453,370.

FIELD OF THE INVENTION

The present invention relates to a phospholipid dependent prothrombin activator, to a method for its purification, and to a test for the detection of Lupus Anticoagulant using the activator.

BACKGROUND OF THE INVENTION

The lupus anticoagulant (LA) is an immunoglobulin (IgG, IgM, or a mixture of both) which interferes with one or more of the in vitro phospholipid dependent tests of coagulation (activated partial thromboplastin time [APTT]; prothrombin time [PT]; dilute Russell Viper Venom Time [dRVVT]). In contrast to specific inhibitors of coagulation proteins, LA has no reactivity with any of the individual Coagulation factors. The name is a misnomer since the vast majority of patients do not have underlying systemic lupus erythematosus (SLE). More commonly, LA is secondary to infections, drugs (e.g. chlorpromazine, quinidine, procainamide) or it may be seen in an autoimmune disease which has recently been described: Primary Antiphospholipid Antibody Syndrome.

Paradoxically, LA is not associated with clinical bleeding unless there is some associated hemostatic defect (e.g. thrombocytopenia). Approximately 30 to 40% of patients with LA have a history of venous and arterial thromboembolic events. For a number of years, there has been much discussion as to whether LA was causative, a consequence, or coincident with thrombosis. More recent work in animal models would suggest that indeed LA is a cause of a thrombotic predisposition. Other clinical-manifestations of LA include recurrent fetal loss, intrauterine fetal growth retardation, and prematurity. Also, LA may be associated with thrombocytopenia or autoimmune hemolytic anemias. Two recent excellent reviews discuss LA and its closely related antibody: anticardiolipin antibodies [Tripleft D. A., Brandt J. T., Lupus Anticoagulants: Misnomer, Paradox, Riddle Epiphenomenon. Hematol. Pathol. 2, 121–143, 1988; Love P. E., Santoro S. A., Antiphospholipid Antibodies: Anticardiolipin and the Lupus Anticoagulant in Systemic Lupus Erythematosus (SLE) and Non-SLE Disorders. Ann. Int. Med. 112, 682–698, 1990].

In most cases, LA is detected serendipitous as a result of an unexplained prolonged APTT and/or PT. Typically, an abnormal APTT is associated with quantitative or qualitative deficiencies in factors XII, XI, IX, VIII, V, or X while PT prolongation generally indicates a deficiency in either factor II, V, VII, X, or fibrinogen. Mixing patient plasma with a source of normal platelet poor plasma will result in lack of correction of the prolonged APTT and/or PT. Lack of correction is a sine qua non for the diagnosis of an inhibitor (synonym circulating anticoagulant).

The diagnosis of LA is often difficult. Commercially available APTT reagents show a wide range of sensitivity to LA and there appears to be differences betwween IgG and IgM LA. In addition to the APTT, other tests have been used to screen for LA including: dilute Russell Viper Venom Time (dRVVT), Kaolin Clotting Time, and dilute APTT. The performance of these tests is difficult requiring mixing patient and normal plasma in the case of the Kaolin Clotting Time and dilute APTT. Consequently, these tests are not readily automated with conventional coagulation instrumentation. Furthermore, if commercial freeze-dried plasmas are used as a source of normal plasma for the mixing studies, there may be false negative results due to a high content of phospholipids in the lyophilized commercial preparations.

Once a patient plasma has been established as having a prolonged screening study with lack of correction by mixing with normal platelet poor plasma, it is necessary to confirm the phospholipid specificity of the inhibitor. Two contrasting approaches have been utilized. The first of these employs a dilute .phospholipid test system (e.g. tissue thromboplastin inhibition [TTI]) to accentuate the inhibitor effect. The second approach utilizes a source of excess phospholipids (e.g. Platelet Neutralization Procedure [PNP]) to "bypass" or "neutralize" the LA. Comparative analysis of these two different approaches suggests the PNP is more sensitive than the TTI.

In addition to the heterogeneity of commercial available reagents, patient plasmas demonstrate remarkable heterogeneity suggesting that there is a family of antibodies with LA activity. The problems of diagnosing LA have been highlighted by the deliberations of the SSC Subcommittee for Standardization of Lupus Anticoagulants (Exner, T. et al., SSC Subcommittee for the Standardization of Lupus Anticoagulants, Guidelines for Testing and Revised Criteria for Lupus Anticoagulants. Thromb. Haemost. 65, 320–322, 1991).

The venoms of several snake species contain enzymes that convert the zymogen prothrombin into the enzyme thrombin and/or its catalytically active precursor meizothrombin. Both activation products convert fibrinogen into fibrin and thereby cause plasma coagulation. Also, both thrombin and meizothrombin catalyze the hydrolytic release of chromophore from synthetic chromogenic thrombin sensitive substrates. Some of these snake venom prothrombin activators do not require a cofactor while a second group depends on the presence of calcium ions and phospholipid. A third group needs factor V in addition to calcium and phospholipid. A review on snake venom prothrombin activators is presented by: Rosing J., Tans G., Thromb. Haemost. 65, 627–630, 1991.

Phospholipid dependent prothrombin activators whose potency is enhanced by phospholipid but not by factor V have been found in the venom of snakes belonging to the Elapidae family, especially members of the Oxyuranus and Pseudonaja genera. A method for the purification of the prothrombin activator from the venom of *Pseudonaja textilis* using chromatography on cancanavalin A-sepharose and gel filtration is described by Masci P. P. et al.; Biochemistry International 17, 825, 1988. A commercial preparation of the activator prepared according to this method is available from Venom Supplies, Tanunda, Australia. The prothrombin activator isolated from *P. textilis* venom according to Masci et al. is a protein with a molecular mass of greater than 200.000 daltons consisting of several non-covalently linked subunits as shown by polyacrylamide gel electrophoresis in the presence of sodium dodecylsulfate (SDS-PAGE). The activator according to Masci et al. (1988) was able to clot citrated plasma in the absence of calcium ions. Its plasma clotting activity was, however, stimulated 2.5 fold in the presence of calcium but no additional stimulation was observed with the addition of phospholipids.

Prothrombin activators which are insensitive to phospholipids can be isolated from venoms of snakes belonging to the family Viperidae, especially from venoms of species belonging to the genera Echis, Trimeresurus, and Bothrops using conventional protein separation techniques as described by R. K. Scopes, Protein Purification, Springer-Verlag, New York, Heidelberg, Berlin, 2nd edition, (1987). A review on the zoological classification of venomous snakes can be found in G. Underwood, Classification and distribution of venomous snakes in the world. In: C. Y. Lee (ed). Snake Venoms p. 15–40, Springer Verlag: Berlin, Heidelberg, New York (1979). A specific method for the isolation of the prothrombin activator from *Bothrops atrox* venom is described by Hofmann H. and Bon C., Biochemistry 26, 772 (1987) and the method for the preparation of ECARIN (phospholipid independent prothrombin activator derived from *Echis Carinatus* venom) venom is provided by Morita T. and Iwanaga S., J. Biochem. 83, 559 (1978). ECARIN activator is commercially available from Pentapharm Ltd., Basle, CH. One ECARIN activator unit is the amount of ECARIN activator which under defined conditions generates one International Unit (U) of enzyme activity from prothrombin as measured with the synthetic chromogenic thrombin substrate Tos-Gly-Pro-Arg-pNA (1 U being the amount of enzyme which hydrolyzes 1 µM of substrate per minute under standard conditions).

SUMMARY OF THE INVENTION

It was found that the clotting time of human citrated plasma following the addition of crude venom from the Australian brown snake *Pseudonaia textilis*, or of the commercially available prothrombin activator from this venom, was slightly shortened by the presence of phospholipid and calcium ions. It was also found that coagulation induced by *P. textilis* venom or by the commercial activator thereof (prepared according to Masci et al.), in the presence of phospholipid and calcium was not significantly delayed in LA containing plasma, as compared to normal plasma. It was then surprisingly found that the venom of *P. textilis* contained two different prothrombin activators, one of which required phospholipids and calcium ions for its action and was sensitive to LA, the second one acted independent from phospholipid and calcium and was insensitive to LA. It was moreover found that the phospholipid dependent prothrombin activator (PLDPA) from *P. textilis* venom was adsorbed to barium sulfate, while the phospholipid-independent prothrombin activator (PLIPA) remained in solution and that a simple purification process for the phospholipid-dependent activator could be based on this behaviour.

It was then found that PLDPA, purified by barium sulfate adsorption, exerted a very low plasma clotting activity in the absence of calcium and that the plasma clotting time measured following the addition of PLDPA in the presence of phospholipid and calcium was strongly prolonged by the presence of LA. It was in addition found that the clotting time, measured following the addition of the ECARIN activator was equal in both normal and LA containing plasma and it was finally found that both PLIPA and PLDPA clotting tests gave normal results with plasma depleted in factor V, VIII or X, respectively.

It is an object of the invention to provide a PLDPA from snake venom which can be used for the determination of LA.

It is another object of the invention to provide a method of purification of the snake venom.

It is still another object of the invention to provide different tests for the determination of LA and test kits which can be used for it.

DESCRIPTION OF THE PREFERRED EMBODIMENTS

PLDPA, free from contaminating PLIPA, is obtainable from aqueous solutions of the crude venom of *Pseudonaja textilis, P. affinis, P. nuchalis, Oxyuranus scutellatus* or *O. microlepidotus*, by 1.) adsorption to a practically water-insoluble barium salt e.g. barium sulfate, barium citrate, barium phosphate or by adsorption to aluminium hydroxide, magnesium hydroxide or tricalcium phosphate, 2.) washing the adsorbate with water or saline to remove non-adsorbed protein, 3.) elution of PLDPA with an aqueous solution of the alkali-, ammonium- or organic amine salt of acids which form practically insoluble salts, complexes or chelates with earth alkali- and aluminium ions e.g. citrate, morpholino ethane sulfonate, phosphate or ethylene diamine tetraacetate and 4.) removal of eluent by ultra-filtration, dialysis or gel filtration. The resulting PLDPA migrated by electrophoresis in the presence of SDS in a gel gradient of 8 to 25% polyacrylamide as one major band with a mobility corresponding to molecular mass of 40,000 to 60,000 Daltons and one or two minor bands with molecular mass between 100,000 and 150,000 Daltons. The plasma clotting activity measured on platelet poor human plasma of PLDPA according to the present invention was stimulated approximately 20 times by the addition of calcium ions and approx. 50 times by the addition of both calcium ions and phospholipid.

A clotting test, sensitive to LA can be carried out by mixing a plasma sample with a suitable amount of a phospholipid suspension and a solution of PLDPA, and by measuring the clotting time upon the addition of a sufficient amount of calcium chloride solution. The PLDPA clotting time is prolonged in LA containing plasma as compared to normal plasma; it is also prolonged in case of a quantitative or qualitative prothrombin abnormality, but it remains unaffected by deficiencies in factors V, VII, VIII, IX or X.

The clotting test can be simplified by the preparation of a reconstitutable reagent which contains PLDPA and phospholipid in a stable, co-lyophilized form. If desirable, the amount of calcium ions required for this test can also be co-lyophilized with PLDPA and phospholipid, if a non-hygroscopic calcium salt with a low freezing point depressor activity e.g. calcium gluconate or calcium lactobionate is used.

A chromogenic test for LA can be performed by mixing a plasma sample with PLDPA and phospholipid, adding calcium chloride, incubating this mixture for a defined activation time, quenching the prothrombin activation process by the addition of a chelating agent e.g. ethylene diamine tetraacetate containing buffer and measuring the generated amount of thrombin by means of a chromogenic substrate e.g. Tos-Gly-Pro-Arg-pNA. The amount of thrombin generated in LA containing plasma is significantly smaller as compared to the amount generated in normal plasma; it is also smaller in case of a qualitative or quantitative prothrombin abnormality.

A clotting test for LA, the result of which is not affected by a prothrombin deficiency, comprises the determination of the plasma clotting time after the addition of a PLIPA e.g. ECARIN, measurement of the clotting time after the addition of phospholipid and of a PLDPA, and calculation of the PLIPA/PLDPA clotting time ratio and/or the PLDPA/PLIPA clotting time ratio. Both PLIPA and PLDPA clotting times are inversed proportional to the prothrombin content of the plasma sample. However, while LA present in the sample, by interaction with the added phospholipids, causes a prolongation of PLDPA clotting time, the ECARIN activator clotting time remains unaffected. A PLIPA/PLDPA clotting time ratio below 1 or a PLDPA/PLIPA clotting time ratio above 1 (within reference interval) therefore indicates the presence of LA or of prothrombin with a molecular abnormality. The potency of PLIPA and PLDPA reagents according to the present invention is with preference adjusted in such a way that both reagents clot normal human plasma under defined conditions within the same time e.g. 20 seconds. The reagents for the PLIPA- and PLDPA test can be prepared in a liquid form with a limited stability, to be used within a limited time period or can be manufactured as stable, freeze dried preparations to be reconstituted with water or buffer to obtain the ready-for-use solution.

An immunochromogenic principle for an LA test can be carried out by coating a microtiter plate with phospholipid, adding a series of normal and patient plasma samples into the wells (to bind LA to the phospholipid layer), removal of plasma by rinsing, addition of a PLDPA and calcium-containing prothrombin solution to each well, quenching the activation by the addition of a chelating agent, adding a synthetic chromogenic thrombin substrate, quenching the reaction with acetic acid after a defined incubation period and measuring released chromophore by means of a microtiter plate reading photometer. This test principle is not affected by prothrombin abnormalities.

By the incorporation of prothrombin as the substrate for PLDPA in any of the above test methods, an interference by qualitative and/or quantitative prothrombin abnormalities can be avoided.

Phospholipids suitable for the performance of the PLDPA tests are preparations containing phosphatidylethanolamine (Synonym: colamine kephalin) and phosphatidylserine (Synonym: serine kephalin) which are obtainable from animal, plant or microbial biomass by organic solvent extraction. Suitable phospholipid preparations e.g. from bovine brain, egg yolk or soy bean are commercially available from Sigma Chemical Company, St. Louis, Mo., USA.

A stable, PLDPA reagent for reconstitution is obtainable by dissolving PLDPA purified according to the present invention and a protein-stabilizing polymer e.g. a collagen derived polypeptide and/or bovine serum albumin and/or dextran in water or buffer, adding a phospholipid suspension and freeze-drying this mixture after subdivision into vials suitable for reconstitution. If desirable, a lyophilizable calcium salt e.g. calcium gluconate or calcium lactobionate can be added.

A stable, PLIPA reagent for the PLIPA test according to the present invention is obtainable by dissolving ECARIN activator and a stabilizing polymer e.g. serum albumin and/or a collagen derived polypeptide and/or dextran in water or in a buffer solution and freeze-drying this solution subdivided into vials suitable for reconstitution.

The pH of the test reagents is adjusted to 7 to 8 preferentially to 7.4 and stabilized by means of a buffer system. Suitable buffer systems comprise for example tris-(hydroxymethyl)-aminomethane hydrochloride (TRIS-HCl), 2-(N-morpholino)ethane-sulfonic acid (MES) and N-2-hydroxy-ethylpiperazine-N'-ethane-sulfonic acid (HEPES).

The PLIPA and PLDPA tests for LA in plasma can be carried out by measuring the time until onset of fibrin formation in the reaction mixture by manual or mechanical detection of gel formation or by photometric turbidity measurement.

EXAMPLE 1

Preparation of PLDPA from *P. textilis* venom 50 mg crude *P. textilis* venom was dissolved in 100 ml aqueous tri-sodium citrate solution. 8 ml barium chloride solution, 1M, were added, the mixture was stirred for 30 minutes, the formed precipitate was separated by centrifugation and dissolved in 33 ml of an aqueous solution of citrated saline (sodium chloride, 0.15M and tri-sodium citrate 0.02M). 2.64 ml of barium chloride, 1M, were added to the solution and after 30 min. stirring, the formed precipitate was separated by centrifugation and the sediment was washed with 33 ml citrated saline. The washed sediment was dissolved in EDTA 0.2M, pH 7.4, and EDTA-barium chelate was removed by ultrafiltration through a membrane with a cut-off of 10,000 Daltons and extensive washing with saline. The retentate was lyophilized to yield PLDPA which migrated in SDS-PAGE, using a gradient of 8 to 25% polyacrylamide, as one major band at a mobility corresponding to a molecular mass of 53,000 Daltons and two minor bands showing a molecular mass of 110,000 to 130,000 Daltons, respectively. A PLDPA solution adjusted to clot normal human citrated plasma in the presence of calcium chloride, 12.5 mM, and rabbit brain phospholipid, 17 µg/ml, within 20 seconds, showed a plasma clotting time in the absence of calcium ions and phospholipid of >900 seconds.

EXAMPLE 2

Preparation of a TEXTARIN activator reagent for testing phospholipid-dependent prothrombin activation Textarin prepared according to example 1 was dissolved in a solvent mixture consisting of 1% collagen-derived polypeptides (Prionex™, Pentapharm) in 0.05 molar HEPES buffer pH 7.4, to make 50 ml of stock solution I. TEXTARIN is Pentapharm AG's trademark for the prothrombin activating component of *Pseudonaja Textilis* snake venom used for the Lupus Anticoagulant test of this invention. It is referred to generically herein as "PLDPA". PRIONEX is a polypeptide fraction for the stabilization of proteins.

500 mg rabbit brain kephatin were homogenized in 5000 ml solvent mixture to obtain stock solution II.

Serial dilutions of stock solution I were prepared by mixing with stock solution II: The clotting time of citrated normal human plasma was then measured with each dilution using the following procedure: 0.1 ml dilution and 0.1 ml calcium chloride solution 0.025M were incubated for 3 minutes at 37° C., 0.1 ml normal human plasma was then added and the clotting time was measured manually. A mixture of 1 volume stock solution I and 64 volumes stock solution II clotted normal plasma within 20 seconds. The total amount of PLDPA stock solution was diluted and mixed with kephalin accordingly, subdivided into 1.0 ml portions, filled into siliconized vials and freeze dried. The freeze-dried product, upon reconstitution with distilled water (1 ml per vial), gave a reagent which clotted citrated normal human plasma within 20±2 seconds in a test mixture composed of 0.1 ml plasma, 0.1 ml Textarin reagent and 0.1 ml $CaCl_2$.

EXAMPLE 3

Preparation of Ecarin reagent for testing phospholipid-independent prothrombin activation 10 mg ECARIN activator with a potency of 500 EU per mg (ECARIN is a Pentapharm AG trademark for prothrombin activator derived from *Echis Carinatus* venom) were dissolved in 50 ml of a solvent mixture consisting of 1% collagen-derived polypeptides (Prionex™, Pentapharm) in 0.05 molar HEPES buffer pH 7.4, to obtain ECARIN activator solution. Serial dilutions of stock solution with solvent mixture were prepared and the clotting time of citrated normal human plasma was measured manually at 37° C. using a test mixture of 0.2 ml plasma and 0.1 ml ECARIN activator dilution. The dilution which clotted normal plasma within 20 seconds was determined and the ECARIN stock solution was diluted accordingly to yield a solution with approx. 16 EU per ml, ready for freeze-drying. The solution was subdivided into portions of 1.0 ml, filled into suitable vials and freeze-dried. The freeze-dried product, after reconstitution with 1.0 ml distilled water, gave a reagent which clotted citrated normal human plasma in 20±2 seconds, in a test mixture composed of 0.2 ml plasma and 0.1 ml ECARIN reagent.

EXAMPLE 4

TEXTARIN activator and ECARIN clotting test for LA

TEXTARIN activator reagent according to example 2 and ECARIN reagent according to example 3 were reconstituted with 1.0 ml distilled water per vial.

TEXTARIN activator and ECARIN clotting times of plasma samples collected from ten pre-operative patients with a normal blood coagulation status and of ten plasma samples containing LA, as verified immunologically, were determined. The results are listed in tables 1 and 2.

TABLE 1

ECARIN activator and TEXTARIN activator clotting times of plasma with a normal clotting status

| Plasma | ECARIN activator ct (sec.) | TEXTARIN activator ct (sec.) | TEXTARIN/ECARIN activators ratio |
|---|---|---|---|
| 1 | 17.3 | 21.2 | 1.23 |
| 2 | 18.7 | 18.0 | 0.96 |
| 3 | 20.2 | 19.5 | 0.97 |
| 4 | 17.1 | 18.1 | 1.06 |
| 5 | 17.1 | 17.9 | 1.05 |
| 6 | 17.0 | 17.6 | 1.04 |
| 7 | 17.4 | 18.6 | 1.07 |
| 8 | 14.6 | 17.9 | 1.23 |
| 9 | 15.8 | 17.4 | 1.10 |
| 10 | 20.6 | 17.5 | 0.85 |

TABLE 2

ECARIN activator and TEXTARIN activator clotting times of LA-containing plasma

| Plasma | ECARIN activator ct (sec.) | TEXTARIN activator (sec.) | TEXTARIN/ECARIN activators ratio |
|---|---|---|---|
| 11 | 17.4 | 27.8 | 1.60 |
| 12 | 13.9 | 34.1 | 2.45 |
| 13 | 19.0 | 24.7 | 1.30 |
| 14 | 14.4 | 40.7 | 2.83 |
| 15 | 16.6 | 38.8 | 2.34 |
| 16 | 18.7 | 41.2 | 2.20 |
| 17 | 20.5 | 75.5 | 3.68 |
| 18 | 21.1 | 90.1 | 4.27 |
| 19 | 14.4 | 28.2 | 1.96 |
| 20 | 15.9 | 58.9 | 3.70 |
| 21 | 22.5 | 38.8 | 1.72 |
| 22 | 17.8 | 75.9 | 4.26 |

EXAMPLE 5

Chromogenic TEXTARIN activator test

Material: Textarin reagent according to example 2 was reconstituted with I ml distilled water per vial. The chromogenic thrombin substrate Tos-Gly-Pro-Arg-pNA (Chromozym TH®, a tripeptide for the determination of proteolytical enzymes manufactured by Pentapharm Ltd., distributed by Boehringer-Mannheim) was dissolved in distilled water at a concentration of 4 μmoles per ml. Calcium chloride/GPRP solution contained 0.025 mmoles $CaCl_2$ and 0.5 mg Gly-Pro-Arg-Pro (GPRP, Pefabloc FG®, an inhibitor of fibrin polymerisation, Pentapharm) per ml. EDTA-buffer was glycine-NaOH buffer, 0.3M, pH 8.4, 0.75 mM in $EDTA.Na_2$.

Test: 0.020 ml TEXTARIN activator reagent and 0.020 ml $CaCl_2$/GPRP were pipetted into a photometric cuvette and preheated for 2 minutes at 37° C., 0.020 ml plasma sample were added and incubated for exactly 30 seconds at 37° C. The activation process was quenched by the addition of 1.74 ml EDTA-buffer, 0.200 ml Chromozym TH® were added and the p-nitro-aniline release catalyzed by generated thrombin was recorded with a photometer at a wave length of 405 nm. The difference in absorbance per minute (DA 405/min.) which is directly proportional to the generated amount of thrombin was measured in normal and LA containing plasma samples.

Results: DA 405/min. values of normal plasma varied between 0.07 and 0.1, whereas LA containing plasma samples gave values of 0.02 to 0.06.

EXAMPLE 6

Preparation of phospholipid dependent prothrombin activator (PLDPA) from venom of different snake species Samples of 5 mg each of dried, crude venom from *Oxyuranus scutellatus, O. microlepidotus, Pseudonaja textilis, P. inframaculata* and *P. nuchalis* were dissolved in 10 ml aqueous tri-sodium citrate solution. 0.8 ml barium chloride solution, 1M, was added, the mixture was stirred for 30 minutes, the formed precipitate was separated by centrifugation and dissolved in 3 ml of an aqueous solution of citrated saline (sodium chloride, 0.15M and tri-sodium citrate 0.02M). 0.25 ml of barium chloride, 1M, was added to the solution and after 30 min. stirring, the formed precipitate was separated by centrifugation and the sediment was dissolved in EDTA 0.2M, pH 7.4 to obtain a stock solution for prothrombin activation tests.

Human plasma clotting time was measured with dilutions of each stock solution in the presence and absence of phospholipid and calcium ions. The results are presented in table 3.

TABLE 3

Clotting time of PLDPA from different snake venoms

| Species | dilution of stock soln. | clotting time (sec) Ca/PL present (double determination) | clotting time (sec) Ca/PL absent (double determination) |
|---|---|---|---|
| *O. scutellatus* | 1/200 | 41.2/41.2 | 111.0/112.0 |
| *O mircoleptidotus* | 1/200 | 34.0/34.0 | 151.0/151.0 |
| *P. textilis* | 1/1000 | 26.0/27.0 | 230.0/233.0 |
| *P. inframaculata* | 1/500 | 25.0/25.0 | 112.0/114.0 |
| *P. nuchalis* | 1/500 | 30.0/30.0 | 75.0/74.0 |

We claim:

1. A test kit containing an agent for conducting clotting tests sensitive to Lupus Anticoagulant, the clotting test agent comprising:

a phospholipid-dependent prothrombin activator isolated and purified from the venom of snakes belonging to the Elapidae family, said activator having:
  i) an increased plasma clotting activity in the presence of phospholipids and calcium ions which activity is reduced in the presence of Lupus Anticoagulant;
  ii) the ability to cause clotting in a normal clotting time in the presence of platelet poor plasma having levels of factor V, VII, VIII, IX, or X that are at normal levels;
  iii) the ability to cause clotting in a normal clotting time in the presence of platelet poor plasma having levels of factor V, VII, VII, IX, or X that are below normal levels; and
  iv) showing one major band at a mobility corresponding to a molecular weight of 40,000 to 60,000 Daltons on an SDS-PAGE.

2. The test kit of claim 1, further comprising calcium salts comprising calcium gluconate or calcium lactobionate.

3. The test kit of claim 1, wherein the kit has a pH of about 7–8, and further comprises a buffer.

4. The test kit of claim 3, wherein the buffer comprises tris-(hydroxymethyl)-aminomethane hydrochloride, 2,(N-morpholino)ethane-sulfonic acid or N-2-hydroxy-ethylpiperazine-N-ethane-sulfonic acid.

5. The test kit of claim 1, further comprising a protein stabilizing polymer comprising a collagen derived polypeptide, bovine serum albumin or dextran in water.

6. The test kit of claim 1 wherein the clotting test agent further comprises at least one of a phospholipid, a protein-stabilizing polymer, or a calcium salt.

7. The test kit of claim 6 wherein the clotting test agent further comprises a phospholipid, a protein-stabilizing polymer, and a calcium salt in co-lyophilized form.

8. A method of using the test kit of claim 7 to conduct a clotting test for Lupus Anticoagulant, wherein the clotting test agent is mixed with a plasma sample to form a mixture, a calcium salt solution is added to the mixture and clotting time is measured.

9. The method of claim 8, wherein the calcium salt solution comprises calcium chloride.

10. The method of claim 8, wherein a portion of the plasma is mixed with a phospholipid independent prothrombin activator, the plasma clotting time is measured, and a ratio of plasma clotting time for the clotting agent and the phospholipid independent prothrombin activator is measured.

11. The method of claim 10, wherein the phospholipid independent prothrombin activator is isolated from the venom of the family Viperidae.

12. A method of using the test kit of claim 1 to conduct a clotting test for Lupus Anticoagulant, wherein the clotting test agent is mixed with a plasma sample, a phoepholipid independent prothrombin activator, and a calcium salt to form a mixture, the mixture is incubated for a defined prothrombin activation time, a chelating agent is added to the mixture to quench prothrombin activation, and thrombin is measured by means of a chromogenic substrate.

13. The method of claim 12, wherein the phospholipid independent prothrombin activator is isolated from the venom of the family Viperidae, and the calcium salt comprises calcium chloride.

14. The method of claim 12, wherein the chelating agent comprises an ethylene diamine tetra-acetate containing buffer and the chromogenic substrate comprises Tos-Gly-Pro-Arg-pNA.

15. A method of using the test kit of claim 1 to conduct a clotting test for Lupus Anticoagulant, wherein the clotting agent is added to a multi-well microtiter plate which has been coated with a phospholipid and which contains normal and patient plasma samples and a chromogenic thrombin substrate in the wells, the plate is then incubated for a defined activation time, an acid is added to the wells to quench the reaction, and any released chromophore is measured.

16. The method of claim 15, wherein the substrate for the phospholipid-dependent prothrombin activator comprises prothrombin and the phospholipids comprise phosphatidylethanolamine or phosphatidylserine.

17. The method of claim 10, wherein the released chromophore is measured by means of a microtiter plate reading photometer.

18. The method of claim 13, wherein the acid is acetic acid.

* * * * *